(12) United States Patent
Hofmann et al.

(10) Patent No.: US 6,381,795 B1
(45) Date of Patent: May 7, 2002

(54) BRUSH PART FOR ELECTRICAL TOOTHBRUSH

(76) Inventors: Raimund Hofmann; Jorg Hofmann, both of Kreuzstrasse 11, 97892 Kreuzwertheim (DE)

( * ) Notice: Subject to any disclaimer, the term of this patent is extended or adjusted under 35 U.S.C. 154(b) by 0 days.

(21) Appl. No.: 09/431,858

(22) Filed: Nov. 2, 1999

(30) Foreign Application Priority Data

Nov. 2, 1998 (DE) ..................... 298 19 500 U
May 4, 1999 (DE) ........................ 199 20 471
Jun. 15, 1999 (DE) ........................ 199 27 297

(51) Int. Cl.⁷ ............................ A46B 13/02; A61C 17/26
(52) U.S. Cl. ........................................................ 15/28
(58) Field of Search .................... 15/22.1, 28, 29

(56) References Cited

U.S. PATENT DOCUMENTS

| | | | | |
|---|---|---|---|---|
| 5,289,604 A | * | 3/1994 | Kressner | 15/22.1 |
| 5,416,942 A | * | 5/1995 | Baldacci et al. | 15/28 |
| 5,461,744 A | * | 10/1995 | Merbach | 15/22.1 |
| 5,577,285 A | * | 11/1996 | Drossler | 15/28 |
| 5,697,117 A | * | 12/1997 | Craft | 15/22.1 |
| 5,723,132 A | * | 3/1998 | Tseng et al. | 15/167.1 |
| 5,732,432 A | * | 3/1998 | Hui | 15/22.1 |
| 5,836,630 A | * | 11/1998 | Hazeu et al. | 15/28 |
| 6,021,538 A | * | 2/2000 | Kressner | 15/28 |

FOREIGN PATENT DOCUMENTS

| | | |
|---|---|---|
| DE | 3346758 A1 | 7/1984 |
| DE | 3937853 A1 | 5/1991 |

* cited by examiner

*Primary Examiner*—Terrence R. Till
(74) *Attorney, Agent, or Firm*—Nixon Peabody LLP; David S. Safran

(57) ABSTRACT

This invention is a brush part for an electrical toothbrush with a housing (40) that can be connected to a handle (30). This housing has a vertical drill hole (49) and a horizontal drill hole (46); an axle (3) that can be connected to a shaft (2) of the handle (30). This axle can be fit into the vertical drill hole (49) such that it is still turnable. A brush head (80) that can be fit into the horizontal drill hole (46) such that it is turnable; Transfer elements (17, 86) to transfer the rotation of the axle (3) onto the brush head (80). The brush head (80) is set in the horizontal drill hole (46) via a lockable sleeve bearing resulting in a corresponding axial fixation, and/or the axle (3) is set in the vertical drill hole (49) via a lockable sleeve bearing (35, 44, 88).

20 Claims, 12 Drawing Sheets

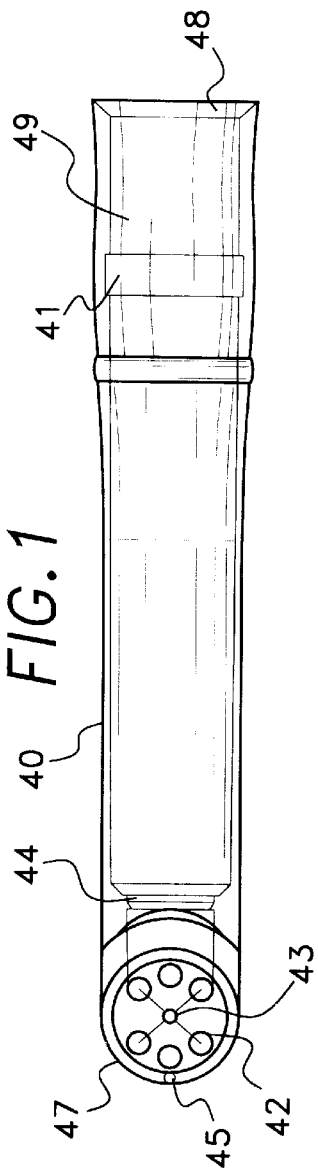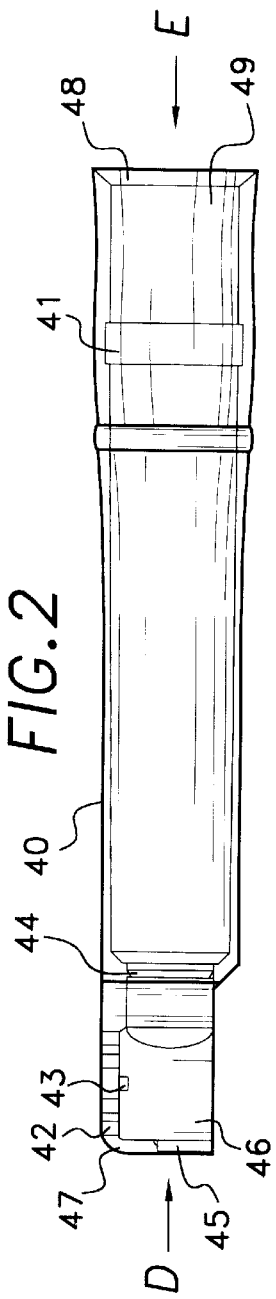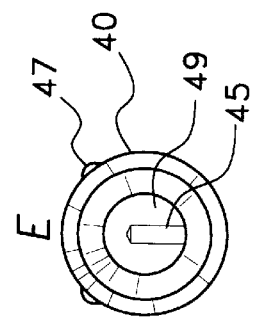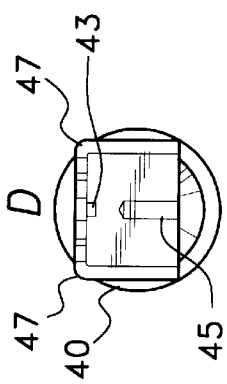

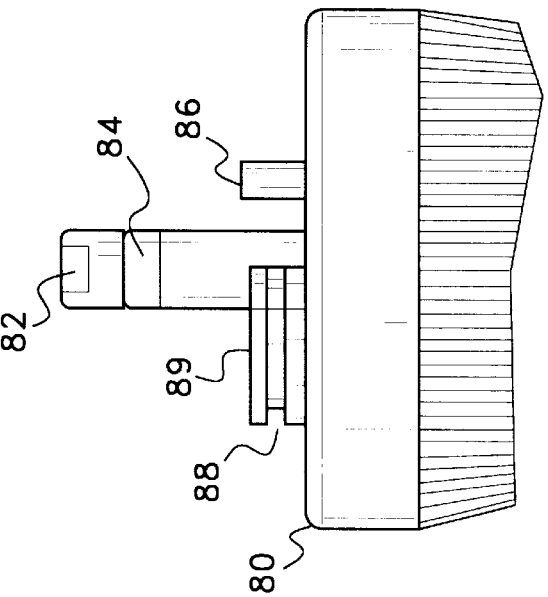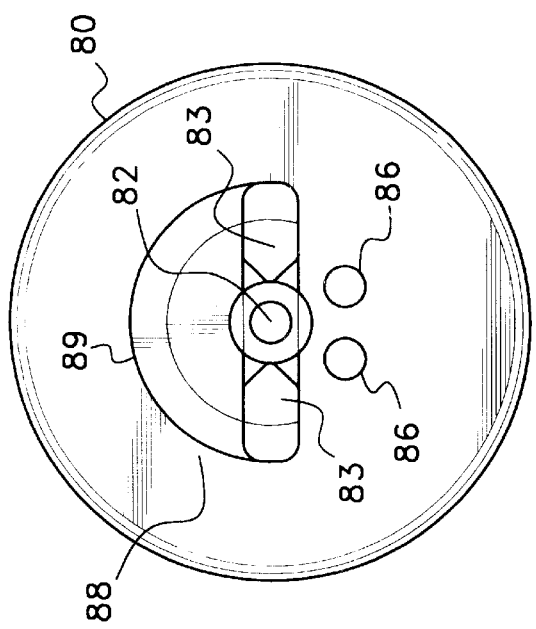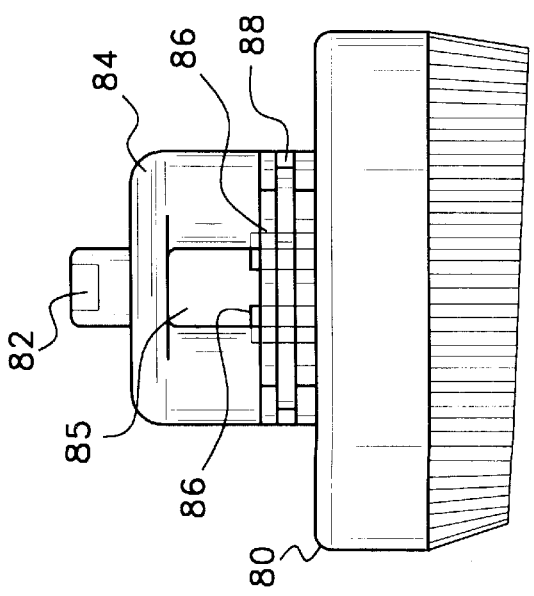

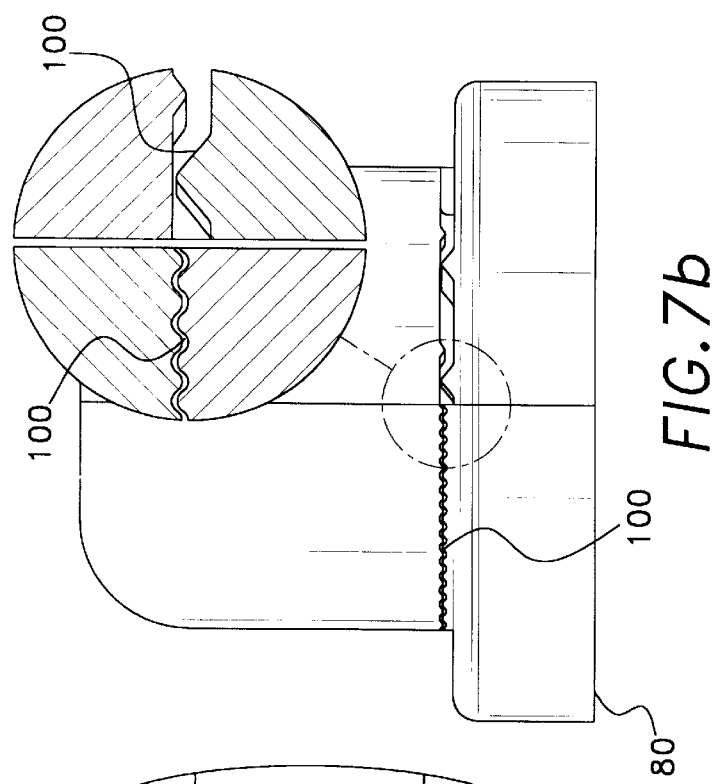
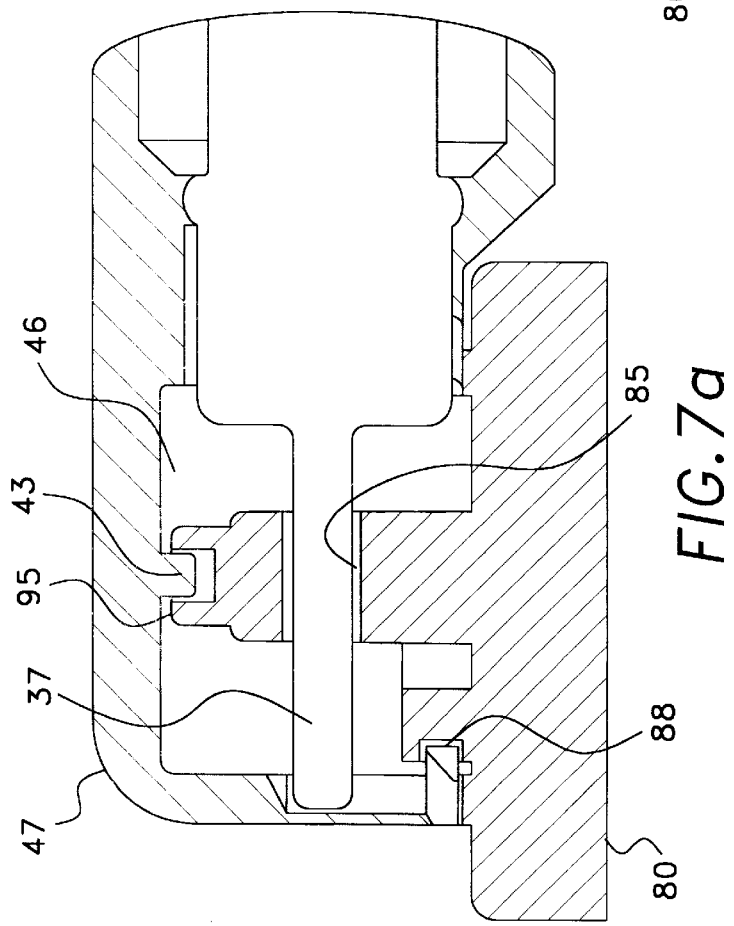
FIG. 7a
FIG. 7b

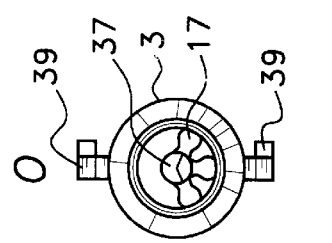
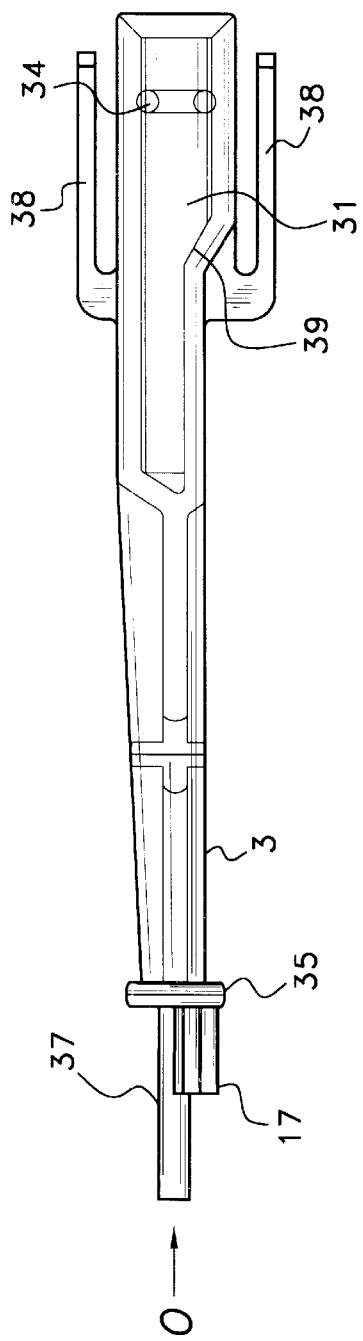
FIG.8b
FIG.8a

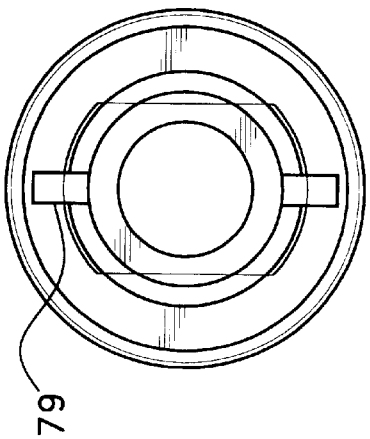
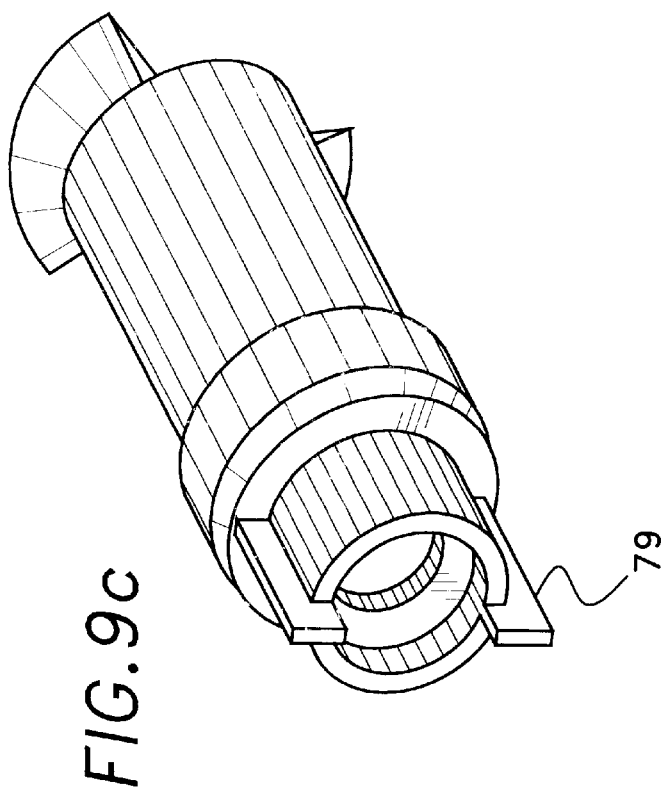
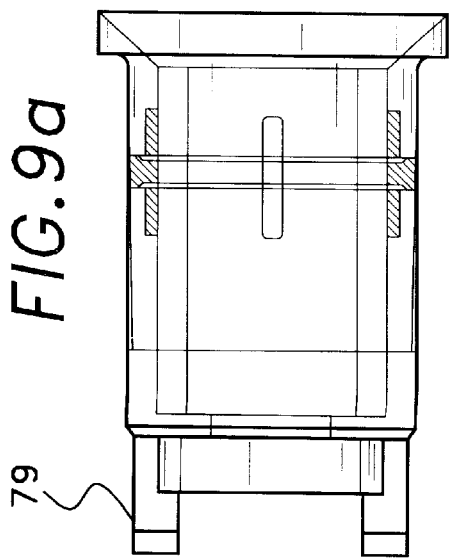

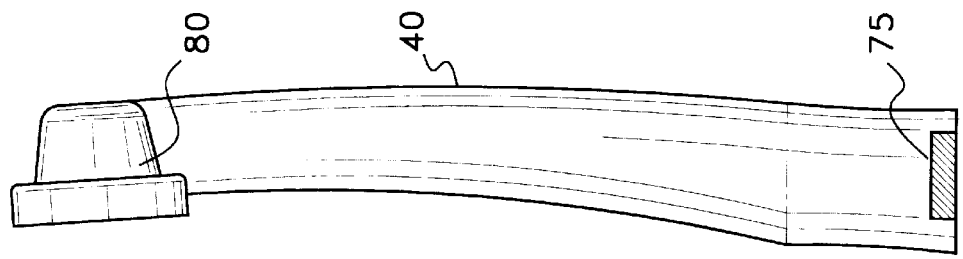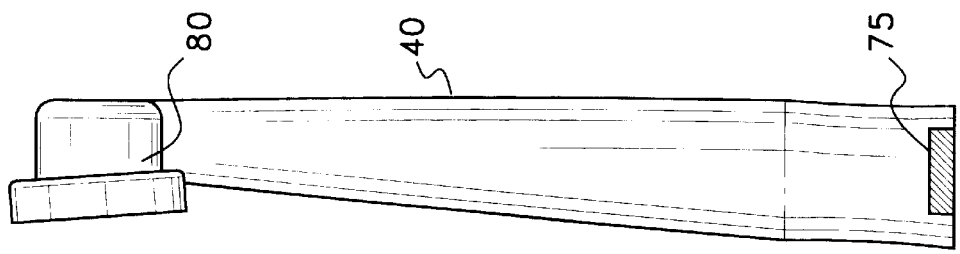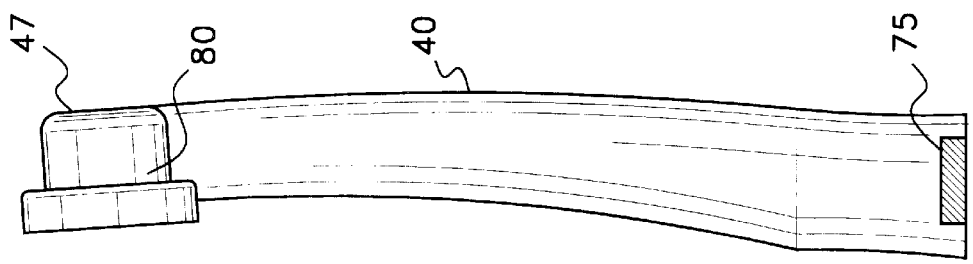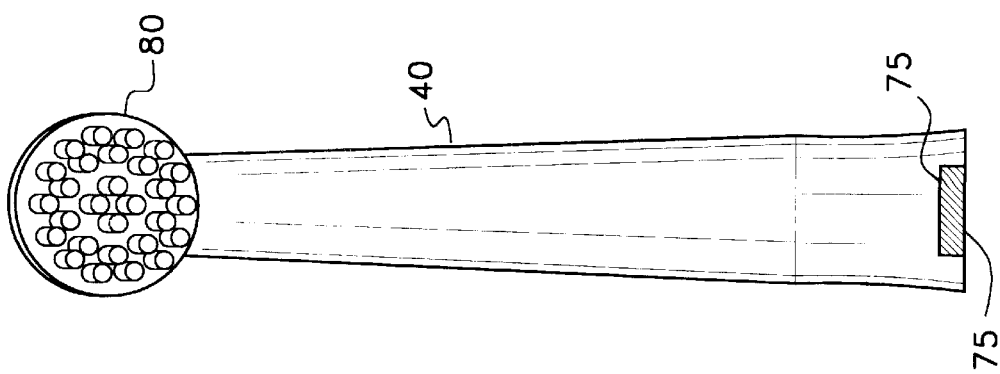

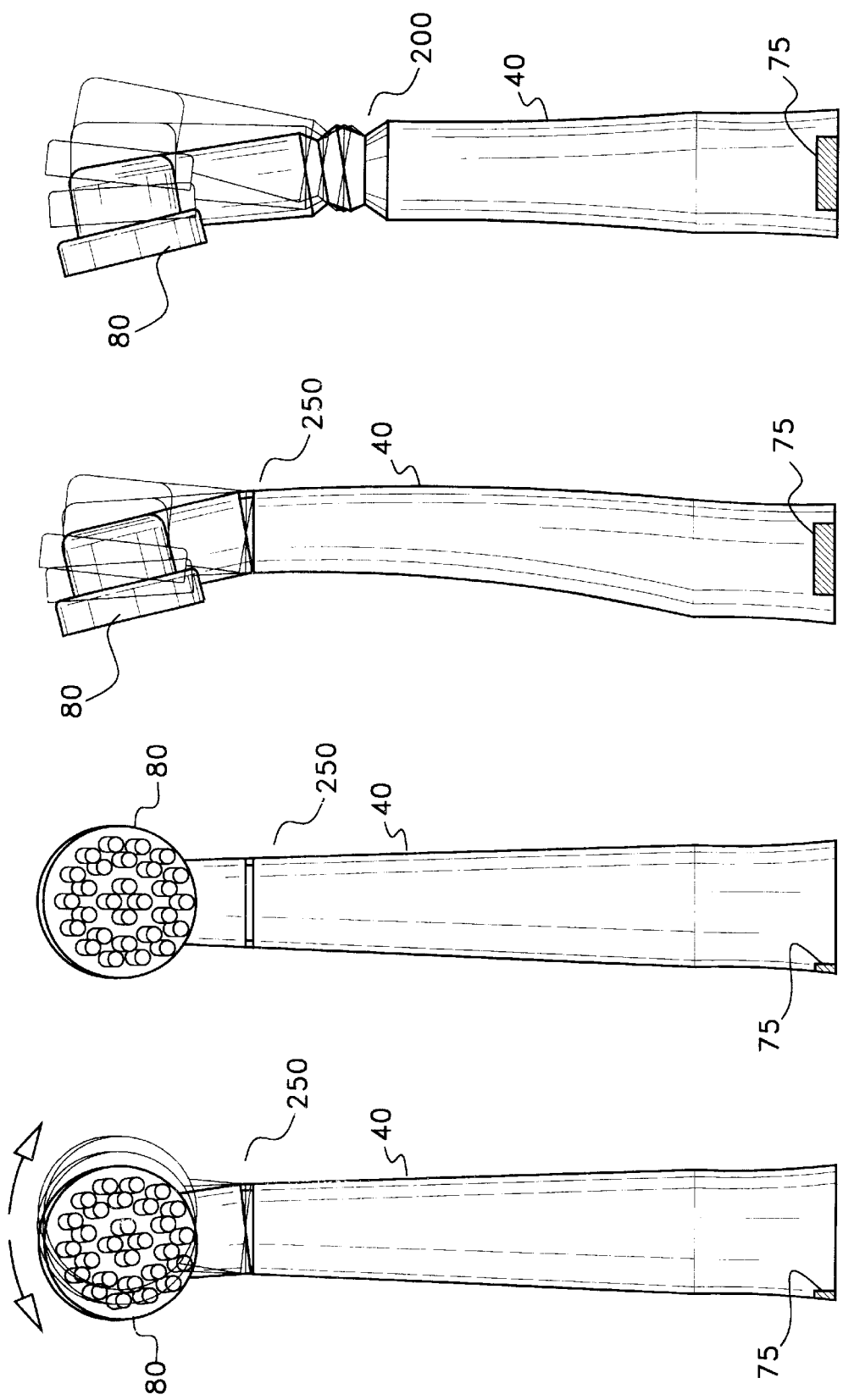

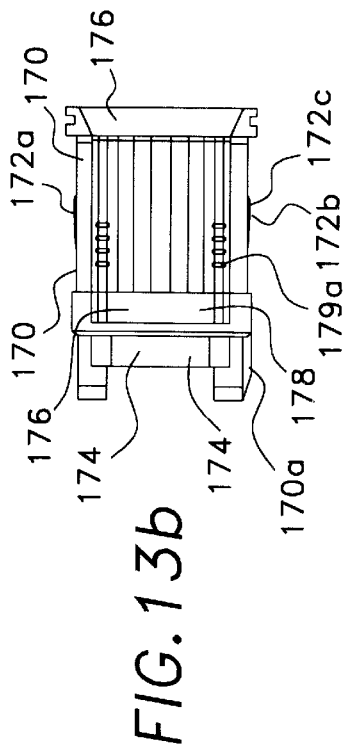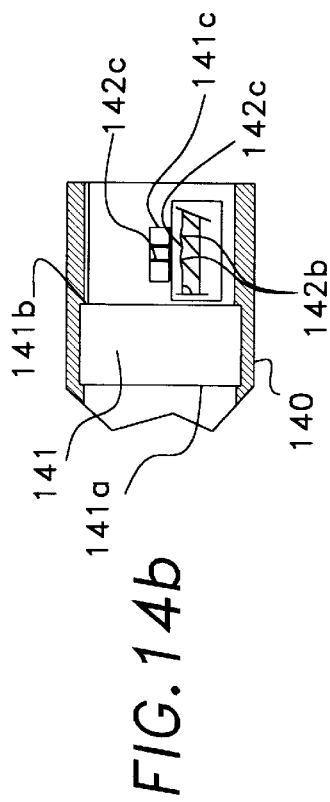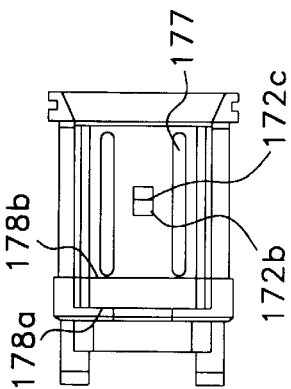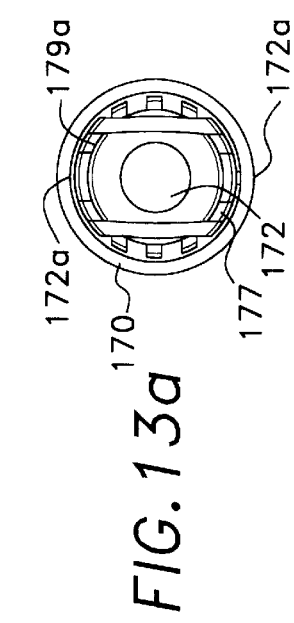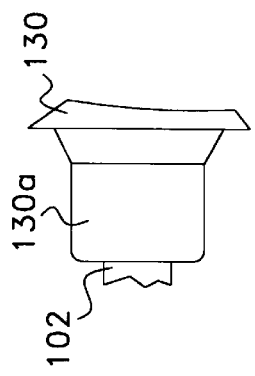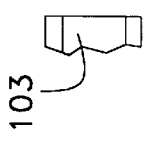
FIG.13b
FIG.14b
FIG.15b
FIG.13a
FIG.14a
FIG.15a

BRUSH PART FOR ELECTRICAL TOOTHBRUSH

BACKGROUND OF THE INVENTION

This invention concerns the head of an electrical toothbrush that is connected to the handle by a housing case which has a vertical and a horizontal drill-hole; an axle, connectable with a shaft of the handle, that can be fit into the vertical drill hole such that it is turnable; a brush head that can be fit into the horizontal drill hole such that it is turnable; transfer elements to transfer the rotation of the axle to the brush head. Such toothbrush parts are widely available nowadays. All known brush parts specifically go with and fit their corresponding handles. Thus, brush parts of a different make cannot be exchanged for that of another, but fit only a given handle. Brush parts on the market consist of different individual parts made from various materials. Usually they are part plastic and part metal. Because of the large number of components, these parts are difficult to assemble and costs are relatively high. Furthermore, the known brush parts are designed such that they cannot be repaired if they break but have to be replaced as a whole.

Growth of microorganisms is facilitated by the moisture remaining in some parts of the toothbrush. To counteract this, bristles are made of oligo-dynamic materials, generally as galvanic coating or mounting devices.

DE 39 37 853 A1 describes an electrical toothbrush that has a handle with an electrical drive inside the drive shaft, as well as a brush part containing an axle in its housing. The handle is connected to the brush head via connecting parts in order to attach the brush to the handle and to establish an attachment between the drive shaft and the axle.

DE 39 37 853 A1 discloses an attachment of the brush part to the handle in axial and radial direction by separate connecting parts. The connecting parts of the drive shaft and the axle, and the connecting parts of the handle and the neck of the brush interact. The axial connection is established by lockable elements of the axle, which act on a counter bearing of the drive shaft. The radial connection works based on a special profile of the housing and the head of the handle.

It is known from DE 33 46 758 A1 that there is supposed to be a bevel gear connection or a toothed rack gear between the brush head and the axle of the brush part.

Commonly available are also complicated tilting lever constructs that transfer the rotation of the axle to the brush head. These constructs are not only difficult to assemble but consist of many individual parts.

A further disadvantage of the known brush heads is the fact that tartar is difficult to remove with rotating bristles.

One of the tasks of this invention is to design a simpler brush part for an electrical toothbrush that can be produced and assembled easier and shows better cleaning action compared to the known brush parts.

In particular, the number of individual components should be reduced. Furthermore, a brush part should be constructed such that it will fit various brush handles of different makes without an additional adapter.

SUMMARY OF THE INVENTION

The invention is a brush part according to claim 1.

The basic idea of this invention is that the brush head is bedded in a horizontal drill hole by a lockable sleeve bearing. This sleeve bearing has a roughened surface allowing for an axial oscillation.

An essential advantage of this invented brush part is that the number of individual components is reduced through integration. The use of one or more sleeve bearings simplifies the assembly. The removal of tartar is greatly enhanced by the axial oscillatory movement that adds to the radial movement of the brush head. This results in a thrusting action of the bristles in such a way that the tartar gets broken up and can be removed easier.

Furthermore, the individual components of the invented brush part can be designed to be replaceable such that, for example, the brush head can be exchanged without having to replace the complete brush part.

The sub-claims describe improvements and developments that can be of advantage for the in claim 1 described brush part.

An additional idea of this invention is to push the brush part over the drive shaft of the handle via a hollow axle. The brush part can be attached in axial direction onto an overhanging housing component using a clamping plug that is movable in axial direction and is moldable due to locking elements. The rotary movement of the metal axle of the handle is transferred by attachment of the axle of the brush part. The radial and axial fixation of the brush part is achieved by attachment via the elastic, moldable plug. Thus, no connecting elements are needed between the metal axle of the handle and the axle of the brush part. Another advantage of this invention is that—should it become necessary to replace the brush part—the customer can exchange individual parts separately without having to replace the entire unit.

BRIEF DESCRIPTION OF THE DRAWINGS

Possible models of the invention are shown in the figures and described in the figure legends.

FIG. 1 A schematic diagram of the housing case of a model of the invented brush part. Top view in the direction of the horizontal drill hole.

FIG. 2 A schematic diagram of the housing case of a model of the invented brush part. Top view in the vertical direction to the horizontal drill hole. FIG. 2a Corresponding top view in direction of arrow D; FIG. 2b corresponding top view in direction of arrow E.

FIG. 5a A schematic diagram of the brush head of a model of the invented brush part in side view of bridge, FIG. 5b top view of bridge, FIG. 5c side view parallel to bridge.

FIG. 7a An enlarged schematic diagram of the brush head of a model of the invented brush part in side view of bridge, FIG. 7b simplified version to illustrate the action of the roughened surface of the sleeve bearing.

FIG. 8a A schematic diagram of the axle of a different model of the invented brush part in side view, FIG. 8b top view in direction of arrow O.

FIG. 9a A schematic diagram of the locking ring of an additional model of the invented brush part in cross section, FIG. 9b corresponding top view in direction of arrow P, FIG. 9c corresponding 3-dimentional perspective diagram FIGS. 10a–h Examples of various potential forms of the brush part.

FIGS. 13a–b A schematic diagram of the clamping plug of the brush part with elongated, lockable clamping elements on top and bottom, and rips on top and bottom working in radial direction.

FIG. 14a A schematic diagram of the housing case of a model of the invented brush part in cross section in vertical cross section, FIG. 14b horizontal cross section with respect to clamping plug.

FIGS. 15a–b A schematic diagram of the clamping plug of the brush part. Top view of clamping plug with elongated, lockable clamping elements displaced to the right, up to the inside edge of the housing case.

DETAILED DESCRIPTION OF THE PREFERRED EMBODIMENTS

Figure 3C:
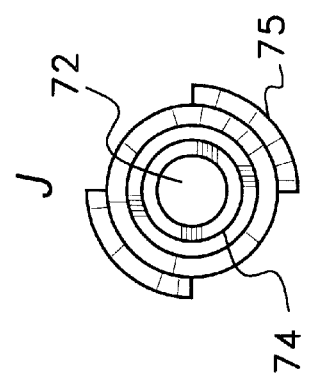
FIG. 3a A schematic diagram of the locking ring of a model of the invented brush part in cross section, FIG. 3b top view in direction of arrow I, FIG. 3c top view in direction of arrow J, FIG. 3d corresponding 3-dimentional perspective diagram.
Figure 3D:
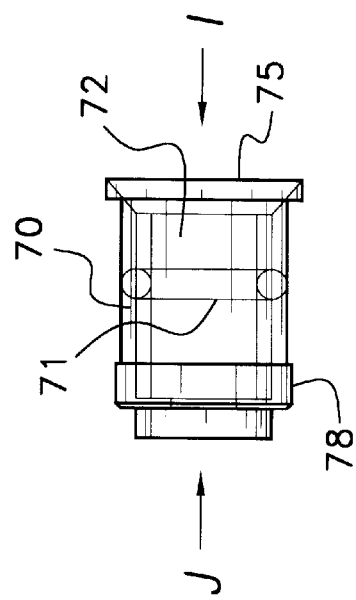

With regards to the figures: Denotations (numbering) of components or components of the same function, are kept consistent throughout the figures.

FIG. 1 shows a schematic diagram of the housing case of a model of the invented brush part. Shown is a top view in the direction of the horizontal drill hole. FIG. 2a shows a schematic diagram of the housing case of a model of the invented brush part. Top view in the vertical direction to the horizontal drill hole. FIG. 2a is a corresponding top view in direction of arrow D; FIG. 2b is a corresponding top view in direction of arrow E.

40: housing or housing case; 41: a circular cut-out for a bulge 78 (see FIG. 3); 42 holes; 43: pin; 44: cut-out for bulge 35 (see FIG. 4); 45: flute or drill hole; 46: horizontal drill hole; 47: frontal portion; 48: space for protrusion 75 (see FIG. 3); 49: vertical drill hole.

The housing 40 of this model of the invented brush part is a single plastic injection part which has the vertical drill hole 49 in its interior, extending from the back end to the front portion 47. In the hind portion is the circular flute 41 that is used to lock a locking ring described later.

Together with the corresponding bulge, the cut-out 44 is used to snap-lock an axle that fits into the housing 40. At this place, the cross section of the horizontal drill hole narrows. The cut-out 44 has a circular edge ensuring the bulge of the axle to lock in radial direction but allowing for an axial rotation of the axle without restriction.

Vertically to the vertical drill hole 49 is the horizontal drill hole 46. The bottom of the drill hole shows holes 42 for cleaning of the housing by toothpaste and water such that no residue remains that could hinder the function of the brush or help the accumulation of germs. The horizontal drill hole 46 serves to fit the brush head described later. At the bottom of the horizontal drill hole is a place for pin 43 that fits into the corresponding bushing of the brush head.

On the wall of the horizontal drill hole 46 at the front section 47 of the housing 40 is a flute 45 for the pin-like extension of the axle.

Figure 3A:
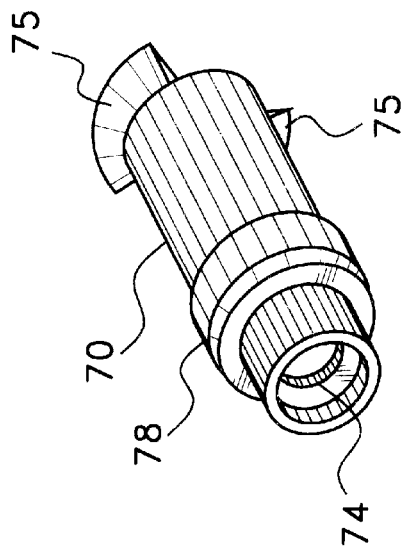
Figure 3B:
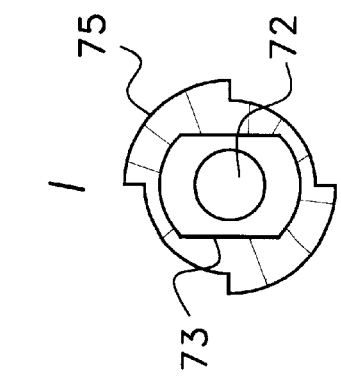

FIGS. 3a to 3d show a schematic diagram of the locking ring of a model of the invented brush part. FIG. 3a shows a cross section, FIG. 3b a top view in direction of arrow I, FIG. 3c a top view in direction of arrow J, and FIG. 3d a corresponding 3-dimensional perspective diagram.

In addition to the already identified components are the following: 70: locking ring; 71: elastic circular and or segmented moldable piece; 72: interior space or interior drill hole; 73: flattened portion; 74: bushing; 75: protrusion; 78: bulge.

FIGS. 3a to 3d show a locking ring 70 that can be inserted and locked into the rear part of the housing 40. To lock all together, a radial bulge 78 exists which snaps into the cut-out 41 of the housing 40. At the rear end of the locking ring are two protrusions 75 which fit snugly into the corresponding hollows 48 of the housing. On the front of the locking ring 70 is a space for a bushing 74 which fits the bottom portion of the axle described below.

As can be seen in FIG. 3a, the hollow space 72 of the locking ring is a space for an elastic moldable piece which interacts with the handle top 30 of a handle that needs to be inserted there. The inside drill hole 72 displays a flattened portion 73 that fits a corresponding flattened portion of the head part 30 such that a radial rotation in opposite directions is inhibited.

The protrusions 75 display a different color to that of the rest of the locking ring 70 so that—when in use—the housing 40 is identifiable by different colors for different users.

Figure 4A:
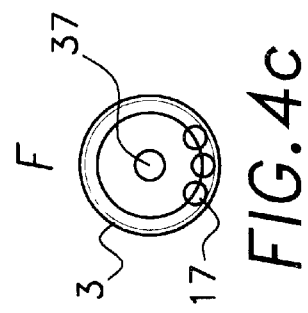
FIG. 4a corresponding top view in direction of arrow G, FIG. 4b sectional view in direction of arrow A, FIG. 4c corresponding top view in direction of arrow F.
Figure 4B:
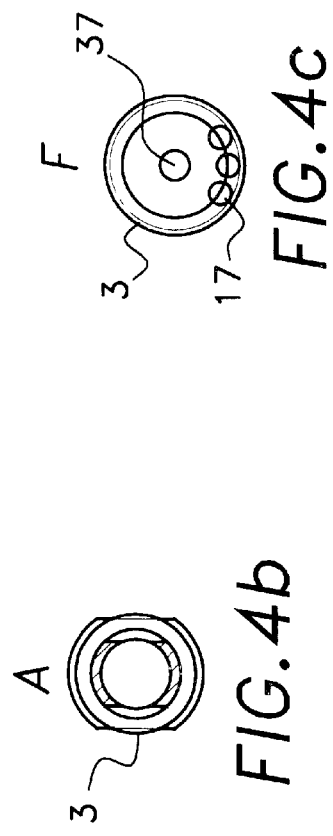
FIG. 4 A schematic diagram of the axle of a model of the invented brush part.
Figure 4C:
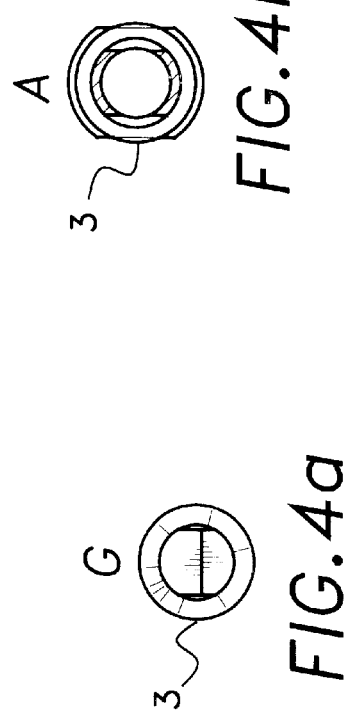
Figure 4:
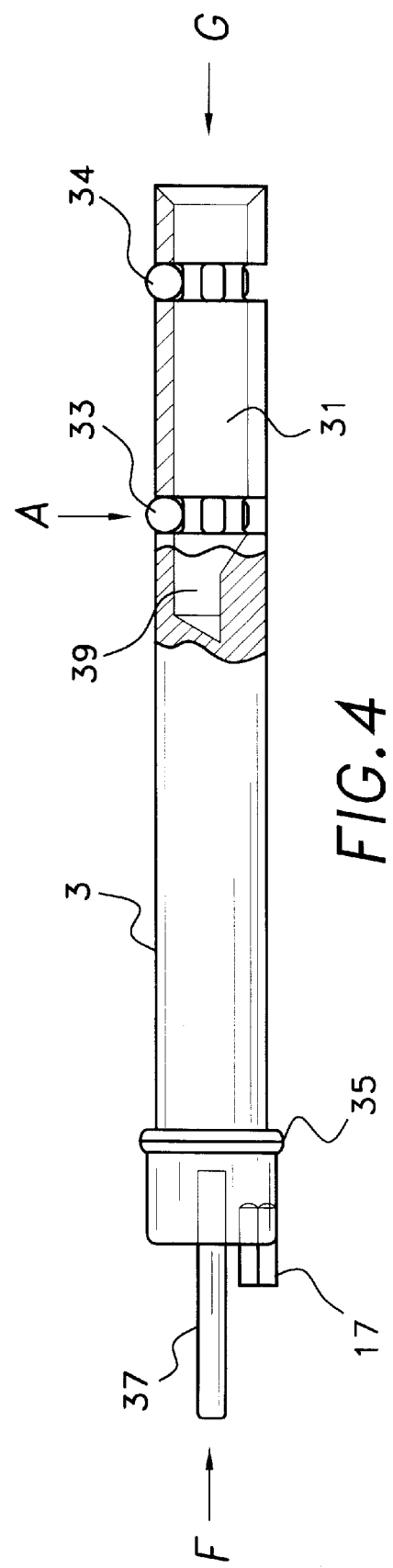

FIG. 4 shows a schematic diagram of the axle of a model of the invented brush part. FIG. 4a shows a corresponding top view in direction of arrow G, FIG. 4b a sectional view in direction of arrow A, and FIG. 4c a corresponding top view in direction of arrow F.

In addition to the already identified components are the following: 3: axle; 33 and 34: elastic moldable piece in form of two locking rings and/or clamping segments; 35: bulge; 37: pin; 17 toothed rack; 31: hollow; 39: angled portion.

Axle 3 of this model shown in FIG. 4 is also a single plastic injection part for which, however, a different plastic material is used for the elastic moldable pieces 33 and 34. Bulge 35 snap-locks into the cut-out 44 of the housing 40 when inserted, such that a locked sleeve bearing is formed. The toothed racks 17 of the front end interact with corresponding toothed racks found on the brush head described later. At the rear end of axle 3 is a hollow or drill hole 31 where an engine shaft of a corresponding handle can be inserted.

The hollow 31 contains an angled portion 39 at the front end that corresponds to a transition of the engine shaft from a full-circular-profile to a semi-circular profile. Thus, the engine shaft is axially fitted snugly in its front portion. Fitted at the rear portion of the axle in a two-component plastic injection molding step, are elastic rings 33, 34. These affect the engine shaft in an elastic clamping way such that an axial fixation is possible. Especially the front ring 33 is meant to be constructed such that it fits into a commonly used notch of the engine shaft 2. The elasticity of the fitted parts differs from that of the axle 3 since the possibility of a flexible fitting is bigger.

Looking from an axial point of view, that is from points F or G, one can notice that the axle 3 has essentially a circular symmetry.

Although the pin 37 of this model and the axle 3 are made as a single plastic injection molding part, the pin could also be made as a separate metal pin for better durability. The pin 37 is supposed to lock the brush head 80 in axial direction of the horizontal drill hole 46 when assembled.

FIG. 5 shows a schematic diagram of the brush head of a model of the invented brush part. FIG. 5a is a side view of the bridge, FIG. 5b a top view of the bridge, and FIG. 5c a side view parallel to the bridge.

In addition to the already described components: 80: brush head; 81: bristles; 82 bushing for the pin 43; 83: stops; 84: bridge; 85: hole for the pin 37; 86: toothed racks; 88: flute; 89: semi-circular rib.

The brush head 80 shown in FIG. 5 displays bristles on one side that are attached by gluing or that are mechanically braided in.

Opposite of the bristles 81 on the brush head 80 is a bridge 84 that creates a hole 85 when assembled, where the pin 37 of the axle 3 can be inserted.

The stops 83 serve as a boundary for the rotation and have a built-in fin 89 that is semi-circular. The stops 83 push against the pin-like elongation 87 of the axle 3 in their final assembled state.

There is a bushing 82 on the top side of the bridge 84 in which the pin 43 of the front piece 47 of the housing 40 fits in.

As can be seen in FIG. 5c, there is a flute 88 in the rip 89 into which an overhanging edge of the horizontal drill hole 46 can fit (not shown in any figure) in order to create a lockable sleeve bearing.

The toothed racks 86 interact with the toothed racks 17 of axle 3.

Figure 6:
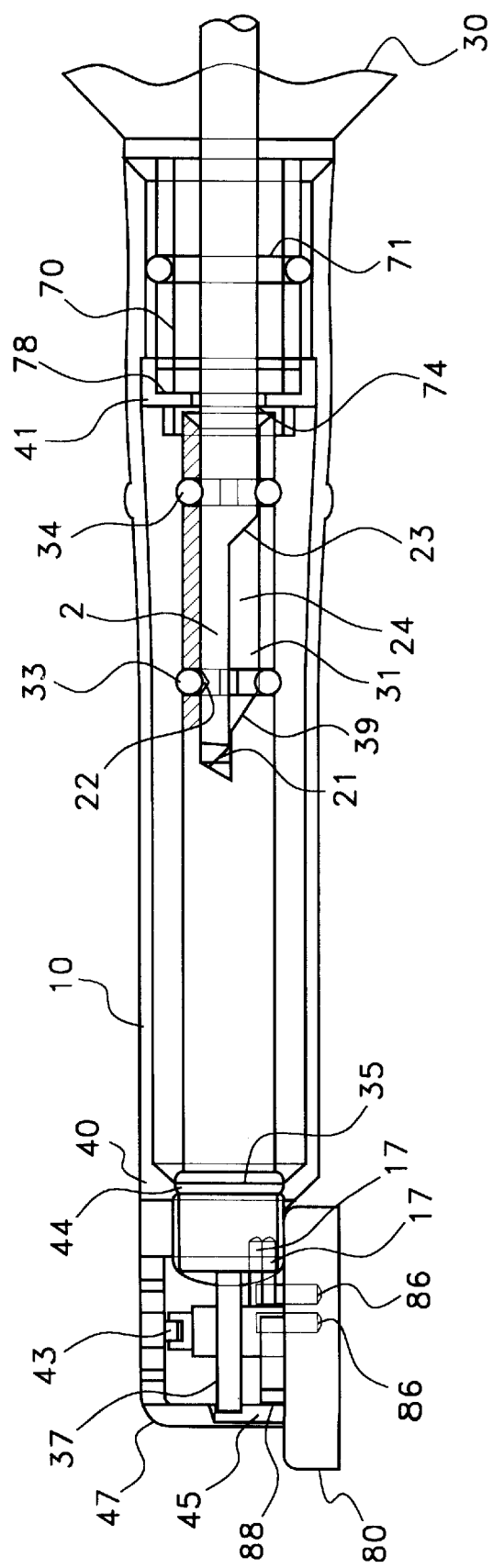
FIG. 6 A schematic diagram of a completed model of the invented brush part fit on top of a corresponding handle.
Figure 12:
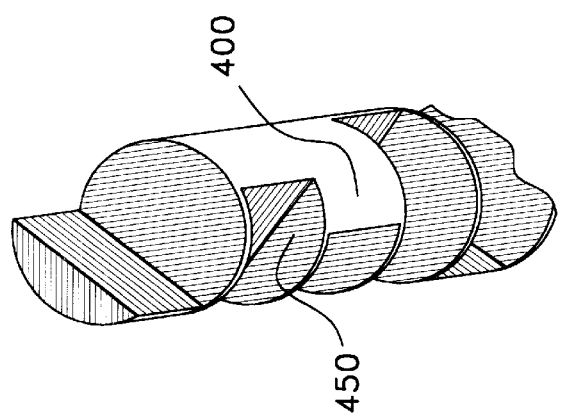
FIG. 12 Perspective view of the Cardan joint in FIG. 11c.

FIG. 6 shows a schematic diagram of a completed model of the invented brush part that fits on top of a corresponding handle.

In addition to the already described components: 2: engine shaft; 21: angled portion; 22: notch; 23: full-circular profile; 24: semi-circular profile; 10: whole brush part; 30: head of handle.

For clearness reasons, not all previously defined components are marked in FIG. 6.

In connection with FIG. 6, the assembly and the function of the invented brush part model are described.

First the brush head 80 is fitted into the frontal portion 47 of the housing 40 and locked with the top edge (not shown) by the flute 88. Thus, the head 80 is bedded in a sleeve bearing at the frontal portion, and can rotate. Next, the axle 3 is inserted from the rear end of the housing 40 such that the bulge 35 is locked into the cut-out and the pin 37 extends through the hole 85 of the bridge 84 up to the flute 45. Thus, together with both stops 83, final positions for the rotation of the brush head 80 are defined in the frontal portion 47 of the housing 40. Furthermore, the two toothed racks 17 in the frontal portion of the axle 3 snap into position with the two toothed racks 86 integrated in the brush head. Thus, the rotation of the axle 3 is transformed into a vertical (with respect to the axle) rotation of the head 80.

The locking ring 70 is installed in the rear portion of the housing 40. In this way, the rear end of the axle 3 fits into the bushing 74 of the locking ring and can rotate.

With these three assembly steps, the invented brush part model is easily assembled and taken apart. Most importantly, it is possible to disassemble the brush part without technical knowledge in order to replace the brush head 80.

The head of the handle 30, together with the overhanging engine shaft 2, is put into the locking ring 70. The orientation is given by the flattened part 73 of the locking ring. Thus, the engine shaft 2 ends up in the hollow 31 of the axle 3 and is held in axial direction by the elastic ring insertions 33, 34. Above the angled portion 39 is the semi-circular sector of the shaft 2, fitting the hollow such that an exact transformation of the rotation onto the axle 3 is ensured. The frontal ring 33 fits into the notch 22 of the shaft 2. As can be seen in the figure, this assembly makes it possible to fit engine shafts of various thickness and lengths as well as of various geometric designs. In addition, the head 30 of the handle is locked into position by an elastic ring 71 in order to avoid an axial movement.

FIG. 7 shows an enlarged schematic diagram of the brush head of a model of the invented brush part. FIG. 7a is a side view of the bridge, and FIG. 7b is a simplified version to illustrate the action of the roughened surface of the sleeve bearing.

From FIG. 7a one can see the locking of the brush head 80 in the horizontal drill hole 46 via the lockable sleeve bearing—here in the form of a projection fitting into flute 88. This results in an axial fixation.

As shown in FIG. 7b, the created sleeve bearing displays evenly roughened surfaces 100 that are directed toward each other and have the effect that an axial oscillation of the brush head 80 in the horizontal drill hole 46 is made possible.

As can be seen in the enlargements, the roughened surfaces of the described model have projecting elements—especially teeth or arches—that are evenly spaced. The arrangement of the projecting elements is designed such that the frequency of oscillation is in the ultrasound range.

The roughened surface could also be put instead/as well in sector 90 in FIG. 7a, that is on the bushing for pin 43.

FIG. 8 is a schematic diagram of the axle of a different model of the invented brush part. FIG. 8a is a side view, and FIG. 8b a top view in direction of arrow O.

For this model, the assembly of the engine shaft 2 is improved. It is possible in the previous model that the brush head 80 has to be turned for assembly with respect to the engine shaft 2, since the angled portion 21 does not overlap exactly with the angled portion 39.

To improve this fitting, axle 3 has two oppositely spaced wings 38 on either side.

FIG. 9 is a schematic diagram of the locking ring of an additional model of the invented brush part. FIG. 9a is a cross section, FIG. 9b a corresponding top view in direction of arrow P, and FIG. 9c a corresponding 3-dimentional perspective diagram.

At the end of locking ring 70, that is directed to the housing 40, there are two pins 79 that result in a set back action when turned from the central position, since the wings 38 deform when the axle 3 is turned.

If the engine shaft 2 is removed, the potential tension is set free, and the wings 38 turn the axle 3 and thus the brush head 80 to the central position. This makes it easier to reinstall the engine shaft 2 into axle 3.

Known and commonly used manual toothbrushes are sometimes angled, resulting in a better fit of the toothbrush with respect to the teeth. Often, manual toothbrushes also have a flexible neck, which supposedly further improves this adjusted fit. Such a design is so far non-existing for brush heads of electrical toothbrushes.

FIGS. 10a through 10h show models of the invented brush part containing such a flexible sector.

In addition, the colored protrusions 75, that make it possible to differentiate between different brush parts for various users, are widened divided asymmetrically. This makes the brush parts easily distinguishable in any and all positions.

In FIGS. 10a and 10b, the brush head 80 with the frontal portion 47 has been angled altogether, while in FIG. 10c, only the head 80 with the bristles has been angled. In FIG. 10d, the form of the housing has been bent banana-like.

In FIG. 10e, the housing 40 has an elastic sector 200 in the transition portion to the frontal portion 47. This makes it possible that the frontal portion 47 can be angled at various degrees with respect to the brush head 80 simply be exerting pressure on it.

In FIG. 10f there is—instead of the elastic sector 200—a single-axial ball joint 250 between the housing case 40 and the frontal portion 47.

In FIG. 10g the brush part of FIG. 10f is turned 90 degrees.

The angled movements of the front part of the brush can therefore be copied for the shaft 2 of the drive of the electrical toothbrush without any problem.

The Cardan joint 400, which is made by a multiply displaced, slit-open, and angled sector, makes up for the displaced axle by bending. The bending is possible due to the individual slots 450 and/or the cylindrical sectors, where by the stretching of the material(s), that is bendable without resulting in lasting deformation, cannot be overstepped. Plastics made specifically for this purpose are available on the market, such as Polypropylene.

Figure 11A:
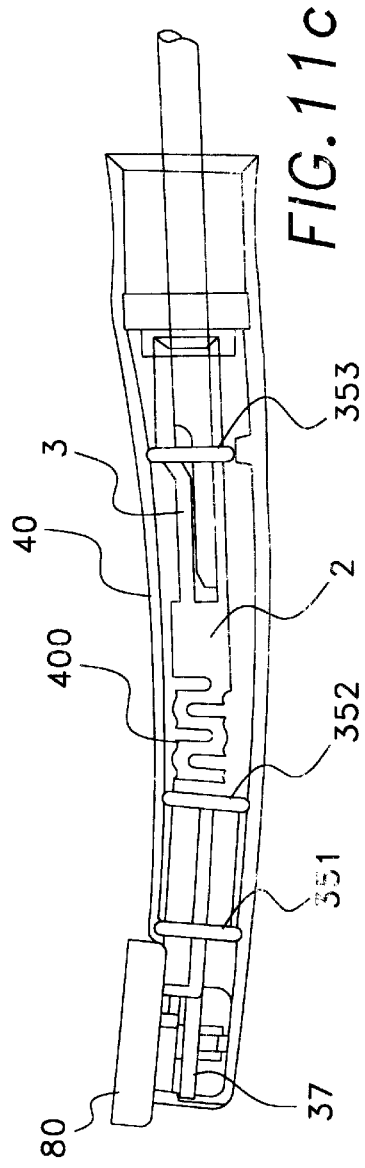
FIGS. 11a–c A schematic diagram of yet another assembled model of the invented brush part.
Figure 11B:
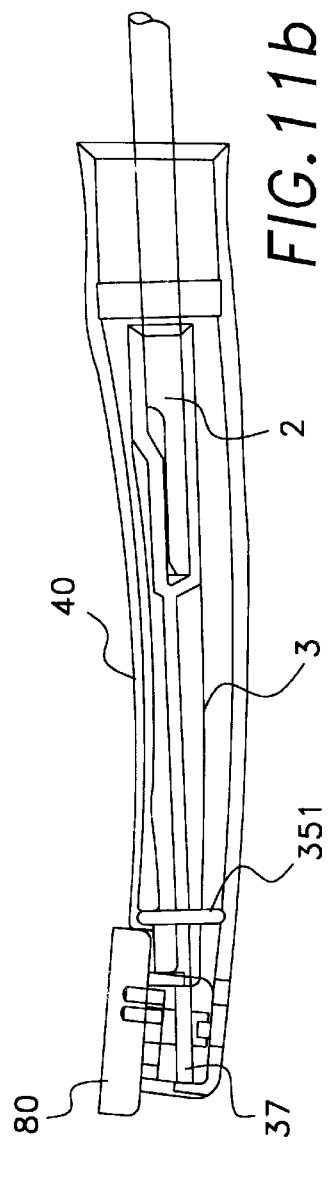
Figure 11C:
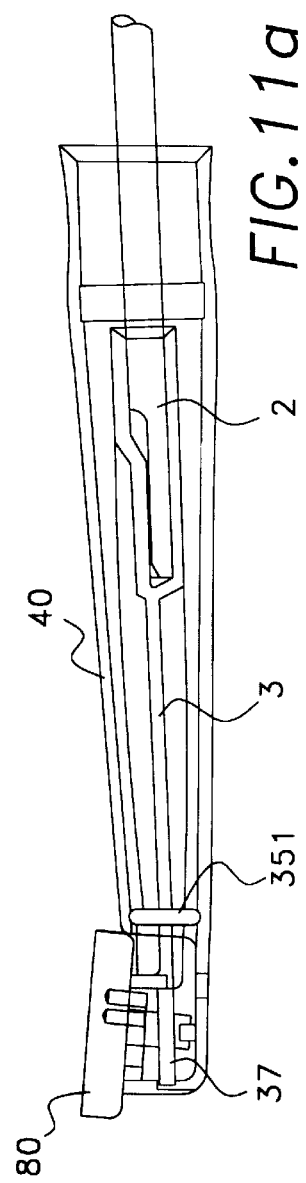

The elastic sector 200 (see FIG. 10e) which is not shown in FIG. 11c, will be constructed such that the Cardan joint 400 will be at its center. The adjustment of the axle is therefore easily possible in one or more directions due to the Cardan joint 400.

The Cardan joint, made from a cylindrical basal part, is made up of parallel slots that are arranged in opposite directions. The depth of the slots is dependent on the material. The bottom of the slots has to be carefully rounded to avoid damage due to tension. During assembly, one should take care that the size of the bearing increases in diameter from the side of the head that contains the horizontal drill hole to the end of the housing. The inside space of the housing 40 has to be big enough that the various components of the bearing can be slid in and assembled easily. Sideways movements of the axle 3 are acceptable during assembly, but in the completed models, the bearing should be aligned properly according to the rotation.

In FIG. 11c, the central pin 37 of axle 3, containing the head 80, is not aligned. This misalignment of the axle results in burdening the pin 37 as well as the head 80 in the region of the hole. This misalignment is however tolerable considering how long the brush heads last. The misalignment can be eliminated with the Cardan joint 400. Alternatively, instead of a single component axle 3 with Cardan joint 400, a multi-component axle with a single or multiple Cardan joint, could be built.

Although this invention has been described for mainly one preferred model, it is not limited to this model but can be altered in many ways.

Especially the locking ring at the end of the housing is not absolutely necessary. An elastic component set into the housing could take its function. In this case, it would be necessary to bed the end of the axle, facing the shaft, with little room in the vertical drill hole.

Although drill holes are mentioned throughout these descriptions, it should be clear that these holes are not made by drilling but by plastic injection molding.

The rotation between the axle and the brush head cannot only be achieved with the above-mentioned toothed racks, but also with bevel wheels or with a push rod.

Due to the sleeve bearing the axle snap-locks into the cut-out in the housing and is axially fixed. To improve the sleeve bearing, the bulge of the axle can be made of a different material from that of the actual axle. It is possible to mold a different material here by combined plastic injection.

It is also possible that the pin-like elongation of the axle can be fit through the bridge into the axle from the top of the horizontal drill hole. This type of fitting is well known but is mostly applied to hold a stop in position.

FIG. 13 shows a schematic diagram of the clamping plug 170 of the brush part with elongated, lockable clamping elements on top and bottom. These clamping elements act in radial direction compared to the inside edge of the cut-out 141a with handle 130, metal axle 102, and housing cone 130a. 170: clamping plug; 172a: moldable circular or segmented clamping element; 172: interior space; 172b: angled portion; 172c: bulge or flute; 174: bushing; 176: circular elongation; 177: one or more hollows or slots; 178: bulge.

FIG. 14 shows a schematic diagram of the housing case of a model of the invented brush part in cross section. FIG. 14a is a vertical cross section, and FIG. 14b is a horizontal cross section with respect to clamping plug.

140: housing; 141: broadened circular cut-out for a bulge 178 (see FIG. 1); 141c: moldable circular or segmented clamping element; 142b: angled section; 142c: flute or bulge; 149: vertical drill hole.

FIG. 15 is a schematic diagram of the clamping plug 170 of the brush part. Top view of clamping plug with clamping elements 172a displaced to the right up to the inside edge of the cut-out 141b of the housing case 140. 103: axle of brush part.

As can be seen in the figures, the clamping plug 170 will be inserted into the housing 140. The clamping plug 170 is moveable within the broadened circular cut-out 141 between the inside edges 141a and 141b.

If the clamping plug 170 stands on the inside edge 141b of the housing 140 with its bulge edge 178b, the clamping elements 172a and 141c are not in use. Thus, the interior space 172 is open and the clamping plug 170 can easily be pushed open and taken off of housing 130 housing cone 130a.

If the clamping plug 170 is on the inner edge 141a of the housing 140 with its bulge edge 178a, the clamping elements 172a and 141c are in use. Thus, the interior space 172 is caught and smaller, and the clamping plug 170 can only be pushed open or removed by force from the housing 130 or housing cone 130a. Through proper design of the clamping elements 141c, 172a it is possible to adjust the removal of brush part from the handle 130, 130a exactly.

For this purpose, the angled portions 142b of the housing 140 and the angled portions 172b of the clamping plug 170 are adjusted such that the clamping plug 170 is easily moved within the housing 140 in the cut-out 141. During insertion of the clamping plug 170 in the housing 140, the interior space 172 becomes reduced, thus clamping the brush part onto the housing 130, 130a.

To counteract an unintended opening of the mounting, the housing 140 has a flute or corresponding bulge 142c and 172c on the clamping element 141c, and the clamping plug 170 has the same on the clamping element 172a. The flutes and bulges snap-lock the housing 140 together with the clamping plug 170, when the inside edge 141 a is brought to the edge of the bulge 178a.

The brush part is easily removable from the handle by overcoming the resistance of the locking of bulge and flute 142c and 172c by pulling on the brush part, then removing housing 140 from housing 130, 130a, and thus removing the clamping by the clamping elements 141c and 172a.

The clamping plug 170 can have one or more ribs or rib segments 179a in the interior space 172 in order to improve its claiming to housing 130, 130a.

Analogous to the oscillating axle, axles with stroke—or gyratory movement—can be used to achieve the oscillatory movement of the preferred model a corresponding adaptor can be used that is fastened onto the housing 130, 130a in an identical fashion. Alternatively, the brush part can be correspondingly fastened onto its housing, which corresponds to housing 130, 130a.

The clamping plug 170 can have slots 177 for easier and more correct adjustment of the clamping power through the clamping elements 141c and 172a.

To counteract an unintended twisting of the clamping plug 170 in the drill hole 149 of the housing 140, the clamping plug (170) has one or more ribs 170a that act on corresponding spaces 140a of the housing 140 in the drill hole 149.

What is claimed is:

1. A brush part for an electrical toothbrush, said brush part comprising:
   a housing for connection to a handle of the electrical toothbrush, said housing having a vertical drill hole and a horizontal drill hole;
   an axle for connection to a shaft of the handle, said axle being mounted for rotation in the vertical drill hole of the housing;
   a brush head, said brush head being mounted for rotation in the horizontal drill hole of the housing;
   transfer elements for transferring the rotation of the axle to the brush head; and
   a locking ring, said locking ring sized to be received into the housing opposite the horizontal drill hole, said locking ring having a bushing for holding a basal end of the axle.

2. A brush part according to claim 1, further comprising a lockable sleeve bearing formed by a bulge (78) on said locking ring, said bulge being received in a cut-out (41) on said housing, thereby connecting the bushing and the end of the axle to said housing.

3. A brush part according to claim 2, wherein said sleeve bearing for the brush head has roughened surfaces in the horizontal drill hole of the housing such that axial oscillatory movement of the brush head is possible in the horizontal drill hole.

4. A brush part according to claim 3, wherein the roughened surfaces include protruding teeth or arches that are evenly spaced from one another.

5. A brush part according to claim 4, wherein the protruding teeth or arches are arranged such that a frequency of oscillatory movements of the brush head is in an ultrasound region.

6. A brush part according to claim 2, wherein said locking ring has a bulge outside that snap-locks into a corresponding cut-out inside of the housing.

7. A brush part according to claim 6, wherein said locking ring has an inner flat portion to fix the handle such that a radial fixation of the housing is achieved at the head.

8. A brush part according to claim 7, wherein said locking ring has at least one elongated protrusion that fits into corresponding hollows at the end of the housing.

9. A brush part according to claim 8, wherein said locking ring has at least one molded element for connection with the brush head, said at least one molded element having an elasticity different from that of the locking ring.

10. A brush part according to claim 9, wherein said at least one molded element effects at least one of a radial and an axial fixation at the head of the handle.

11. A brush part according to claim 10, wherein said locking ring has at least in part a different color from that of the housing.

12. A brush part according to claim 11, wherein said locking ring has a pair of cones and said axle has a pair of wing portions attached on one side which serve to turn back the axle to a central position.

13. A brush part according to claim 12, wherein said brush head is at least partially coated with a heavy metal material.

14. A brush part according to claim 13, further comprising a brush head for holding a plurality of bristles, said brush head and said plurality of bristles being coated with a oligodynamic material.

15. A brush part according to claim 14, wherein said brush head has a rib with a radial flute on a side opposite the plurality of bristles and a protrusion provided in the horizontal drill hole of the housing that acts together with the flute to create a sleeve bearing such that the brush head axially locks into the horizontal drill hole of the housing.

16. A brush part according to claim 15, wherein said brush head has a bushing on the side opposite the plurality of bristles, said bushing fitting a leading pin at the bottom of the horizontal drill hole of the housing.

17. A brush part according to claim 16, wherein said housing includes at least one of an elastic region and a ball joint, said at least one of an elastic region and a ball joint being provided in a transition region at a frontal portion of the housing such that multi-axis bending is possible.

18. A brush part according to claim 17, wherein said axle has a Cardan joint.

19. A brush part according to claim 18, wherein said Cardan joint has an elongated base portion with a plurality of angular, oppositely-bent slots.

20. A brush part according to claim 1, further comprising a lockable sleeve bearing for locking the axle into the vertical drill hole of the housing.

* * * * *